(12) United States Patent  
Tsuruoka (10) Patent No.: US 9,952,228 B2
(45) Date of Patent: Apr. 24, 2018

(54) METHOD FOR DETECTING ADRENOCORTICOTROPIC HORMONE AND ADSORBENT

(71) Applicant: SYSMEX CORPORATION, Kobe-shi, Hyogo (JP)

(72) Inventor: Rena Tsuruoka, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 1377 days.

(21) Appl. No.: 13/739,723

(22) Filed: Jan. 11, 2013

(65) Prior Publication Data

US 2013/0183762 A1   Jul. 18, 2013

(30) Foreign Application Priority Data

Jan. 13, 2012   (JP) ................................ 2012-005547

(51) Int. Cl.
*G01N 33/74* (2006.01)
*G01N 33/68* (2006.01)

(52) U.S. Cl.
CPC ....... *G01N 33/74* (2013.01); *G01N 2333/695* (2013.01)

(58) Field of Classification Search
None
See application file for complete search history.

(56) References Cited

U.S. PATENT DOCUMENTS

| 3,758,324 | A | * | 9/1973 | Barrett | .................. | C08B 31/003 |
| | | | | | | 106/150.1 |
| 2006/0189795 | A1 | | 8/2006 | Van Alstine et al. | | |
| 2010/0087626 | A1 | * | 4/2010 | Ooya | ........................ | A61K 8/65 |
| | | | | | | 530/354 |
| 2011/0143453 | A1 | | 6/2011 | Van Eyk et al. | | |

OTHER PUBLICATIONS

Livesey, J. H. et al. "Prevention of adsorption losses during radioimmunoassay of polypeptide hormones: effectiveness of albumins, gelatin, caseins, Tween 20 and plasma," Clinica Chimica Acta 123 (1982) 193-198.*
Murphy, H. et al. "The low dose ACTH test—a further word of caution.," J Clin Endocrinol Metab. Feb. 1998;83(2): 712-713.*

* cited by examiner

*Primary Examiner* — Yelena G Gakh
*Assistant Examiner* — Michelle Adams
(74) *Attorney, Agent, or Firm* — Sughrue Mion, PLLC (57) ABSTRACT

A method for detecting adrenocorticotropic hormone comprising: bringing a liquid sample containing adrenocorticotropic hormone into contact with gelled casein to adsorb adrenocorticotropic hormone to the gelled casein; and detecting the adrenocorticotropic hormone adsorbed to the gelled casein is disclosed. An adsorbent of adrenocorticotropic hormone comprising gelled casein is also disclosed.

7 Claims, 9 Drawing Sheets

METHOD FOR DETECTING ADRENOCORTICOTROPIC HORMONE AND ADSORBENT

CROSS REFERENCE TO RELATED APPLICATIONS

This is a Non-Provisional Application claiming priority based on Japanese Patent Application No. 2012-005547 filed Jan. 13, 2012, the contents of all of which are incorporated herein by reference in their entirety.

FIELD OF THE INVENTION

The present invention relates to a method for detecting adrenocorticotropic hormone (ACTH) and an adsorbent of ACTH.

BACKGROUND

Various peptides are contained in the blood. Among them, there are peptides having a blood concentration different from the usual blood concentration in the living body in a certain disease state. Such peptides are attracting attention as markers for disease in the field of clinical tests. For example, Simmonds' disease and Sheehan's syndrome caused by the reduced secretion of pituitary hormone can be clinically tested by detecting ACTH as a marker peptide. However, impurities contained in a biological sample to be used for the clinical test may have an influence on the detection of ACTH. Consequently, there is a demand for a method for detecting ACTH which can suppress the influence of impurities in the biological sample.

SUMMARY OF THE INVENTION

The scope of the present invention is defined solely by the appended claims, and is not affected to any degree by the statements within this summary.

Surprisingly, the present inventors have found out that a gel obtained from casein can selectively adsorb ACTH and completed the present invention.

According to a first aspect of the present invention, a method for detecting adrenocorticotropic hormone comprising:

bringing a liquid sample containing adrenocorticotropic hormone into contact with gelled casein to adsorb adrenocorticotropic hormone to the gelled casein; and detecting the adrenocorticotropic hormone adsorbed to the gelled casein.

According to a second aspect of the present invention, an adsorbent of adrenocorticotropic hormone comprising gelled casein.

DETAILED DESCRIPTION OF THE PREFERRED EMBODIMENTS

[1] Method for Detecting ACTH

In the method for detecting ACTH of the present invention (hereinafter also referred to "detection method"), a process of bringing a liquid sample containing ACTH into contact with gelled casein to allow ACTH to be adsorbed to the gelled casein is performed.

ACTH (a hormone composed of 39 amino acids) is secreted from the pituitary gland in the brain and acts on the adrenal cortex to facilitate secretion of adrenocortical hormone.

In the embodiment of the present invention, the ACTH being detected may be a natural ACTH produced in the living body, a peptide produced by cells such as mammalian cells into which the gene coding for ACTH is introduced, insect cells, $Escherichia\ coli$, or a peptide produced by chemical synthesis. Further, the ACTH has a high homology in amino acid sequence between biological species. Accordingly, the origin of ACTH is not particularly limited as long as it is a biological species that produces ACTH. Examples thereof include mammals (e.g., humans, mice, rats, dogs, and rabbits), birds (e.g., ostriches), and fish (e.g., smooth dogfish).

In the embodiment of the present invention, the liquid sample is not particularly limited as long as it is a liquid sample which may contain ACTH. For example, it may be a biological sample. The biological sample includes body fluid. Preferable examples of the body fluid include blood, plasma, serum, and urine. When the liquid sample is any one of the biological samples, the sample may contain a substance capable of binding to ACTH, which is derived from the living body. In the embodiment of the present invention, ACTH in the liquid sample may form a complex with the substance capable of binding to ACTH. The substance which can be bound to ACTH includes albumin.

The ACTH contained in the liquid sample may be the entire length of polypeptide or a fragment thereof. As a fragment of ACTH, a polypeptide having at least an amino acid sequence from the 1st to 24th position of ACTH is preferred.

In the detection method of the present invention, the gelled casein which is used to adsorb ACTH can be produced by gelling casein. Here, the term "casein" means a phosphorus protein which is known as a main component of milk protein. It is known that the casein is composed of three major casein components: $\alpha_s$, $\beta$, and $\kappa$.

In the embodiment of the present invention, the type of casein which is used as a raw material of the gelled casein is not particularly limited. Examples thereof include acid casein, casein sodium, $\alpha_s$-casein, $\beta$-casein, and $\kappa$-casein. The origin of casein is not particularly limited. Usable examples thereof include casein obtained from the milk of mammals such as cows and goats.

The method for preparing gelled casein is not particularly limited as long as it can gelate casein. For example, it includes a method for preparing gelled casein by reacting a solution of casein with a crosslinker. As such a crosslinker, water-soluble carbodiimide (WSC, chemical name: 1-ethyl-3-(3-dimethylaminopropyl)carbodiimide hydrochloride is preferable.

When the WSC is used, the gelled casein can be obtained, for example, in the following manner. First, 0.1 to 20% (w/v) of a casein solution is mixed with 0.1 to 50% (w/v) of a WSC solution at a volume ratio of 1:0.2 to 50. The mixed solution thus obtained is heated at 65 to 200° C. for 5 to 120 minutes to return to room temperature, resulting in formation of gelled casein in the mixed solution. Then, the gelled casein is recovered from the mixed solution by centrifugation, followed by washing with water or an appropriate buffer solution to obtain gelled casein.

In the embodiment of the present invention, the form of the gelled casein is not particularly limited. Accordingly, the gelled casein obtained in the above manner may be suitably processed into a particle form, a membranous form or the like.

In the embodiment of the present invention, the operation of bringing the gelled casein into contact with the liquid sample is not particularly limited. For example, the gelled casein may be added to the liquid sample to bring them into contact with each other, or a dispersion of the particulate gelled casein may be mixed with the liquid sample to bring them into contact with each other.

As for conditions in the contact of the gelled casein with the liquid sample, from the viewpoint of improving the adsorbing efficiency of ACTH, the gelled casein is preferably brought into contact with the liquid sample under the conditions where the pH in the mixture of the gelled casein and the liquid sample is 6.5 or more, preferably from 6.5 to 10. This is based on the fact that the affinity of the gelled casein for ACTH varies depending on the pH, which has been found by the present inventors. A unit configured to adjust the pH is not particularly limited and it can be suitably selected from methods known in the art. For example, the pH can be adjusted by previously adding a buffer having a buffering action at a pH of 6.5 or more to the gelled casein and/or the liquid sample or adding the buffer to a mixture of the gelled casein and the liquid sample.

In the contact of the gelled casein with the liquid sample, conditions other than the pH are not particularly limited. For example, the content ratio of the gelled casein to the liquid sample is from 1:2 to 1:1000 (at a volume ratio), preferably from 1:10 to 1:200. The ambient temperature is from 4 to 60° C., preferably from 4° C. to room temperature, and the contact time is from 5 seconds to 60 minutes, preferably from 30 seconds to 1 minute.

In the detection method of the present invention, the process of detecting the ACTH adsorbed to the gelled casein is performed after the contact of the gelled casein with the liquid sample.

In the process, a unit configured to detect the ACTH adsorbed to the gelled casein is not particularly limited. For example, the gelled casein adsorbed to ACTH is recovered so that the ACTH adsorbed to the recovered gelled casein can be directly detected. Alternatively, the gelled casein adsorbed to ACTH is recovered and the ACTH is allowed to be released from the recovered gelled casein so that the released ACTH can be detected. That is, the detection method of the present invention may further include recovering the gelled casein brought into contact with the liquid sample and allowing the ACTH adsorbed to the recovered gelled casein to be released.

A unit configured to recover the gelled casein may be suitably selected from units known in the art according to the form of the gelled casein used. For example, the gelled casein can be recovered by centrifuging the mixture of the gelled casein and the liquid sample and removing the supernatant.

A unit configured to allow ACTH to be released from the gelled casein is not particularly limited. For example, ACTH can be eluted from the gelled casein by adding any protein denaturant known in the art to the gelled casein recovered. Examples of the protein denaturant include surfactants such as sodium dodecyl sulfate (SDS), urea, and guanidine.

As described above, the present inventors have found the fact that the affinity of the gelled casein for ACTH varies depending on the pH. That is, in the embodiment of the present invention, the contact of the recovered gelled casein with an aqueous medium at a pH of 5.5 or less allows the ACTH adsorbed to the gelled casein to be released into the aqueous medium. A unit configured to adjust the pH is not particularly limited as long as it is a unit which does not prevent the subsequent detection of ACTH. It can be suitably selected from methods known in the art. The aqueous medium is not particularly limited. From the viewpoint of making the operation simpler, it is preferable to use an aqueous medium which can adjust the pH in the mixture of the gelled casein and the aqueous medium to 5.5 or less. Preferably usable examples of the aqueous medium include inorganic acids known in the art (e.g., dilute hydrochloric acid and dilute sulfuric acid), organic acids (e.g., acetic acid solutions), and buffer solutions having a buffering action at a pH of 5.5 or less (e.g., phosphate buffers and Good's buffers).

A unit configured to detect the released ACTH is not particularly limited as long as it is a unit capable of detecting ACTH by distinguishing from other substances. It can be suitably selected from peptide detection methods known in the art. Examples of the detection unit include SDS-PAGE, subsequent gel staining or Western blotting, ELISA, chromatography, and mass spectrometry.

As described above, in the embodiment of the present invention, it is possible that ACTH contained in the liquid sample is selectively adsorbed to the gelled casein, followed by release into an appropriate aqueous solvent. That is, the detection method of the present invention can be used when intending to selectively recover ACTH from a liquid sample and/or when intending to purify ACTH from a liquid sample. Therefore, the scope of the present invention includes a method for selectively recovering ACTH from a liquid sample and a method for purifying ACTH from a liquid sample.

[2] Adsorbent of ACTH

The adsorbent of ACTH of the present invention (hereinafter also referred to as "adsorbent") has a feature of containing the gelled casein and can be suitably used for the detection method of the present invention. That is, the ACTH in the liquid sample can be selectively adsorbed by using the adsorbent of the present invention, similarly to the gelled casein described in the detection method of the present invention. The ACTH to be adsorbed may be a polypeptide having at least an amino acid sequence from the 1st to 24th position of ACTH. Further, the ACTH may form a complex with a substance capable of binding to ACTH such as albumin.

The gelled casein itself contained in the adsorbent of the present invention can be produced in the same manner as described in the detection method of the present invention. That is, the gelled casein can be obtained by reacting a solution of casein with a crosslinker. As such a crosslinker, water-soluble carbodiimide (WSC, chemical name: 1-ethyl-3-(3-dimethylaminopropyl)carbodiimide hydrochloride is preferable.

The form of the gelled casein contained in the adsorbent of the present invention is not particularly limited. From the viewpoint of easy handling, the particle form is preferred. In this case, the adsorbent of the present invention may be in the form of a dispersion prepared by dispersing in water or an appropriate buffer solution. Alternatively, the adsorbent of the present invention may be in the form of a biuret reagent containing gelled casein particles dried by a known method such as freeze drying and water or an appropriate buffer solution for dispersing the particles at the time of usage. The concentration of the gelled casein particles in the dispersion can be suitably set by those skilled in the art. Usually, it is from 1 to 100 mg/ml, preferably from 5 to 50 mg/ml.

The adsorbent of the present invention may contain known additives in the art, in addition to the gelled casein. Examples of the additives include buffer solutions (e.g., phosphate buffers and Good's buffers), protein stabilizing agents (e.g., BSA), and antiseptics (e.g., sodium azide). In the present invention, the affinity of the gelled casein for ACTH changes according to the pH as described above. Thus, it is preferable to contain a buffer solution having a buffering action at a pH of 6.5 or more.

The method for storing the gelled casein contained in the adsorbent of the present invention is not particularly limited, and it may be stored at, for example, 4° C. to room temperature.

The adsorbent of the present invention has a capacity of selectively adsorbing to ACTH as long as it contains the gelled casein produced in the same manner as described in the detection method of the present invention. The capacity can be confirmed by the detection method of the present invention. Alternatively, the adsorption capacity of ACTH may be confirmed as follows. First, a synthesized ACTH peptide solution with a known concentration is mixed with the produced adsorbent. The gelled casein contained in the adsorbent is recovered from the mixed solution thus obtained. The concentration of the synthesized ACTH peptide contained in the remaining solution is measured and the resulting concentration is compared with the concentration before mixing. As the result of comparison, if the concentration after mixing is sufficiently lower than that before mixing, it is determined that the produced adsorbent has a capacity as the adsorbent of the present invention.

Hereinafter, the present invention will be described in detail with reference to Examples, however, the present invention is not limited thereto.

EXAMPLES

Example 1: Evaluation of Adsorption Capacity of Gelled Casein to ACTH (1-24)

(1) Preparation of Dispersion of Various Types of Gel Carriers
<Preparation of Gelled Casein Carrier Dispersion>
Casein sodium (manufactured by Wako Pure Chemical Industries, Ltd.) was dissolved in MilliQ (registered trademark) water (hereinafter simply referred to as "ultrapure water"; Millipore) to prepare a casein sodium solution (50 g/L (5%)). A 5% water-soluble carbodiimide (WSC, manufactured by DOJINDO LABORATORIES) solution (1 mL) and ultrapure water (3 mL) were added to the casein sodium solution (1 mL) to prepare a casein sodium-WSC mixed solution (5 mL) (final concentration of casein sodium: 1%, final concentration of WSC: 1%). The mixed solution was heated at 80° C. for 10 minutes, followed by returning to room temperature to form a gel in the mixed solution. The supernatant was removed with a pipette from the solution containing the gel and the gelled casein was collected. Ultrapure water was added to the collected gelled casein. The mixture was centrifuged at 22200 G for 10 minutes using a centrifuge (CF15RXII, manufactured by Hitachi Koki Co., Ltd.) to allow it to be separated into a supernatant and gelled casein, followed by removal of the supernatant with pipette. The operation was repeated twice to wash the gelled casein. The gelled casein after washing was made into a fine gel carrier by vortexing and pipetting and the resulting carrier was dispersed in ultrapure water (5 mL). The obtained dispersion was a 1% gelled casein carrier dispersion.
<Preparation of Albumin Gel Carrier Dispersion>
The same operation as the preparation of the gelled casein carrier dispersion was performed using bovine serum albumin (hereinafter referred to as "BSA": manufactured by Sigma Aldrich) in place of casein sodium to prepare a 1% albumin gel carrier dispersion.
<Preparation of Gelatin Gel Carrier Dispersion>
Gelatin (manufactured by Wako Pure Chemical Industries, Ltd.) was dissolved in ultrapure water and heated to 80° C. to prepare a 10% gelatin solution (0.5 mL). The solution was cooled at 4° C. for 2 hours to obtain a gelatin gel. Ultrapure water (4.5 mL) at 4° C. was added to the obtained gelatin gel and the mixture was made into a fine gelatin gel carrier by pipetting. Then, a 1% gelatin gel carrier dispersion was prepared.

(2) Evaluation of Adsorption Capacity of Various Types of Gel Carriers to ACTH (1-24)
The 1% gelled casein carrier dispersion (50 µL) prepared in (1) was mixed with a solution of a polypeptide having at least an amino acid sequence from the 1st to 24th position of ACTH (hereinafter referred to as "ACTH (1-24)" (300 µM, 5 µL, manufactured by Biologica Co.) which was labeled with tetramethyl rhodamine (TMR). A 1M Bicine/NaOH buffer solution (pH 9) (10 µL) and ultrapure water (35 µL) were added to the mixture to prepare a mixed solution (100 µL). The final concentration of the gelled casein carrier in the mixed solution was adjusted to 0.5% and the final concentration of TMR-labeled ACTH (1-24) was adjusted to 15 µM. Similarly, the 1% albumin gel carrier dispersion in place of the 1% gelled casein carrier dispersion and the 1% gelatin gel carrier dispersion were used to prepare each mixed solution. The operation of the gelatin gel carrier was performed while cooling so that the gelatin gel was not dissolved in the solution.

These mixtures were centrifuged at 22200 G for 3 minutes using the centrifuge to allow them to be separated into a supernatant and a precipitate. After the centrifugation, the fluorescence intensity of the supernatant at an excitation wavelength of 540 nm and a fluorescence wavelength of 580 nm was measured with a spectrophotofluorometer (F-7000, manufactured by Hitachi High-Technologies Corporation.). The amount of TMR remaining in the supernatant which was not adsorbed to each gel carrier, i.e., the amount of ACTH (1-24) was calculated. A 15 µM TMR-labeled ACTH (1-24) solution not containing the gel carrier was used as a reference. The results are shown in FIG. 1.

Figure 1:
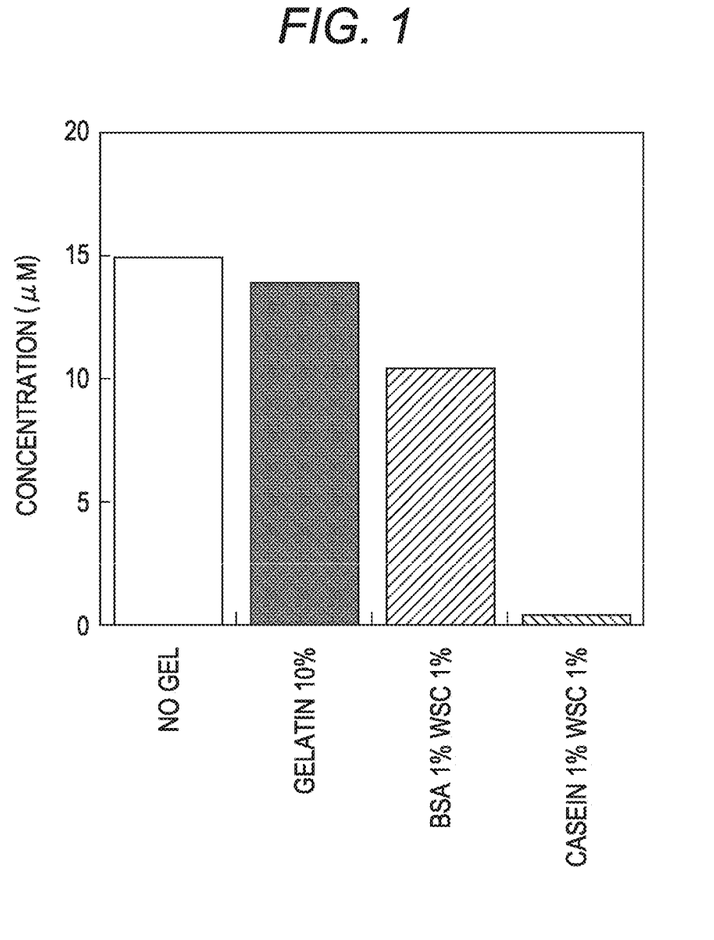
FIG. 1 is a graph showing the adsorption capacity of gel carriers produced from various types of materials to ACTH.

From FIG. 1, it was found that the gelled casein carrier had a high adsorption capacity to TMR-labeled ACTH (1-24) as compared with those of the albumin gel carrier and the gelatin gel carrier.

Example 2: Evaluation 1 of Selectivity of Adsorption Capacity of Gelled Casein Carrier to ACTH (1-24)

(1) Preparation of Mixed Solution of Gelled Casein Carrier and Sample

10 μL of a 1000 μM ACTH (1-24) (manufactured by Biologica Co.) solution, 10 μL of a 1000 μM ITIH4 fragment (manufactured by Biologica Co.) solution, 10 μL of a 1000 μM Fibrinogen α fragment (manufactured by Biologica Co.) solution, and 10 μL of a 1000 μM FactorXIII fragment (manufactured by Biologica Co.) solution were mixed. The 1% gelled casein carrier dispersion (50 μL) prepared in Example 1 (1), a 1M Bicine buffer solution (pH 9) (3 μL), and ultrapure water (7 μL) were added to the mixture to prepare a peptide mixed solution (100 μL). The final concentration of the gelled casein carrier in the peptide mixed solution was adjusted to 0.5% and the final concentration of each peptide was adjusted to 100 μM. The peptide mixed solution thus prepared was centrifuged at 22200 G for 3 minutes using the centrifuge to allow it to be separated into a supernatant and a precipitate, and the supernatant was collected. Ultrapure water (99 μL) was added to the collected supernatant (1 μL) to prepare a 100-fold diluted supernatant. As an index sample for converting the MS concentration, a 1 μM TMR-labeled ACTH (1-24) solution (1 μL) was added to the supernatant to prepare a sample for measuring the peptide adsorption capacity. As a control for comparison with the sample for measuring the peptide adsorption capacity, a control sample was prepared by the same operation as described above using ultrapure water in place of the 1% gelled casein carrier dispersion.

Figure 2:
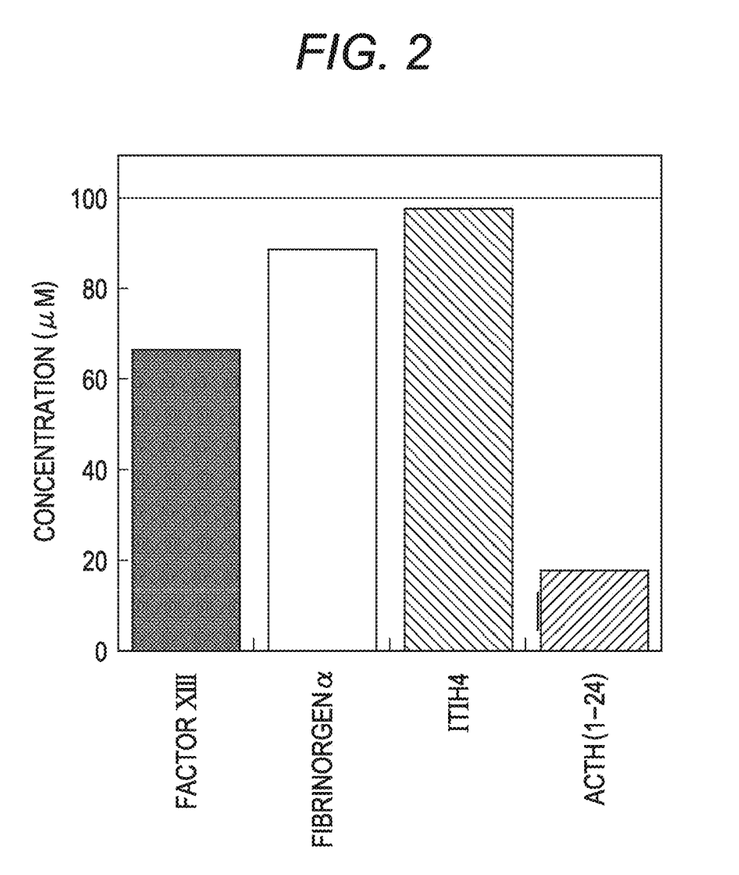
FIG. 2 is a graph showing the adsorption capacity of the gelled casein to various types of peptides.

(2) Evaluation of Selectivity of Adsorption Capacity of Mixed Solution to ACTH (1-24) by MALDI-TOF/MS Measurement In advance, 10 mg/mL of αCHCA solution was prepared as a matrix solution. As a solvent, a solution of 0.1% trifluoroacetic acid/50% acetonitrile was used. Drops of the sample for measuring the peptide adsorption capacity (1 μL) prepared in (1) were put on an MS sample plate and dried under reduced pressure. Thereafter, drops of the matrix solution (1 μL) were put on the plate to be dried. It was confirmed that matrix crystals were formed. The MALDI-TOF/MS measurement (m/z of 800 to 5000) (Voyager-DE (trademark) PRO, manufactured by Applied Biosystems) was performed. The MALDI-TOF/MS measurement of the control sample was performed by the same operation as that of the MALDI-MS of the sample for measuring the peptide adsorption capacity using the control sample in place of the sample for measuring the peptide adsorption capacity. These measurement results were adjusted by the strength of the index sample to calculate the concentration of the peptides contained in the supernatants of each peptide. The results of the adsorption capacity of the gelled casein carrier to ACTH (1-24), ITIH4 fragment, Fibrinogen α fragment, and FactorXIII fragment are shown in FIG. 2. The properties of the peptides are shown in Table 1. In FIG. 2, the solid line of 100 μM shows the concentration of the peptides present in the peptide solution when the gelled casein carrier is not mixed.

TABLE 1

| Peptide name | The number of amino acid residues | Isoelectric point | Adsorption to gelled casein | Amino acid sequence | SEQ ID NO. |
|---|---|---|---|---|---|
| ACTH(1-24) | 24 | 10.6 | + | SYSMEHFRWGKPV GKKRRPVKVYP | 1 |
| ITIH4 fragment | 21 | 12 | − | NVHSAGAAGSRMN FRPGVLSS | 2 |
| Fibrinogen α fragment | 25 | 6.3 | − | DEAGSEADHEGTH STKRGHAKSRPV | 3 |
| Factor XIII fragment | 25 | 3.9 | − | AVPPNNSNAAEDD LPTVELQGVVPR | 4 |

From FIG. 2, it was found that the adsorption capacity of the gelled casein carrier to ACTH (1-24) was significantly high as compared with those to ITIH4, Fibrinogen α, and Factor XIII. This showed that the gelled casein carrier did not adsorb ACTH (1-24) depending on isoelectric points such as acidic, neutral, and basic peptides, but selectively adsorbed ACTH (1-24).

Example 3: Evaluation 2 of Selectivity of Adsorption Capacity to ACTH (1-24) of Gelled Casein Carrier (1) Preparation of Gelled Casein Carrier Dispersion A 1% gelled casein carrier dispersion was prepared in the same manner as described in (1) Preparation of gelled casein carrier dispersion of Example 1.

(2) Preparation of Mixed Solution of Gelled Casein Carrier and Sample

<Preparation of Mixed Solution of Gelled Casein Carrier and TMR-Labeled ACTH (1-24)>

The 1% gelled casein carrier dispersion (50 μL) prepared in (1) was mixed with a 300 μM TMR-labeled ACTH (1-24) solution (10 μL). Further, a 1 M Bicine buffer solution (pH 9) (10 μL) and ultrapure water (30 μL) were added thereto to prepare a mixed solution (100 μL). The final concentration of the gelled casein carrier in the mixed solution was adjusted to 0.5% and the final concentration of TMR-labeled ACTH (1-24) was adjusted to 30 μM. The mixed solution was centrifuged at 22200 G for 3 minutes using the centrifuge to allow it to be separated into a supernatant and a precipitate. As a control for comparison with a mixed solution of the gelled casein carrier and TMR-labeled ACTH (1-24), specifically a mixed solution not containing the gelled casein carrier, a mixed solution for comparison was also prepared by the same operation as described above using ultrapure water in place of the 1% gelled casein carrier dispersion.

<Preparation of Mixed Solution of Gelled Casein Carrier and TMR>

The same operation as the preparation of the gelled casein carrier and TMR-labeled ACTH (1-24) was performed using TMR in place of TMR-labeled ACTH (1-24) to prepare a mixed solution of the gelled casein carrier and TMR. As a control for comparison with a mixed solution of the gelled casein carrier and TMR, specifically a mixed solution not containing the gelled casein carrier, a mixed solution for comparison was also prepared by the same operation as described above using ultrapure water in place of the 1% gelled casein carrier dispersion.

(3) Evaluation of Selectivity of Adsorption Capacity to ACTH (1-24) Based on Fluorescence Intensity Measurement of Mixed Solution <Evaluation of Selectivity of Adsorption Capacity to ACTH (1-24) Based on Fluorescence Intensity Measurement of Mixed Solution of Gelled Casein Carrier and TMR-Labeled ACTH (1-24)>

The fluorescence intensity of the supernatant at an excitation wavelength of 540 nm and a fluorescence wavelength of 580 nm in the mixed solution of the gelled casein carrier and TMR-labeled ACTH (1-24) prepared in (2) was measured with the spectrophotofluorometer (F-7000, manufactured by Hitachi High-Technologies Corporation.). The fluorescence intensity of the mixed solution not containing the gelled casein carrier prepared in (1) as a control was measured. The fluorescence intensity of the control was converted at 30 μM TMR-labeled ACTH (1-24) to calculate the amount of the TMR-labeled ACTH (1-24) which was not adsorbed to the gelled casein carrier and left in the supernatant.

<Evaluation of Selectivity of Adsorption Capacity to ACTH (1-24) Based on Fluorescence Intensity Measurement of Mixed Solution of Gelled Casein Carrier and TMR>

The fluorescence intensity of the supernatant at an excitation wavelength of 540 nm and a fluorescence wavelength of 580 nm in the mixed solution of the gelled casein carrier and TMR prepared in (2) was measured with the spectrophotofluorometer (F-7000, manufactured by Hitachi High-Technologies Corporation.). The fluorescence intensity of the mixed solution not containing the gelled casein carrier prepared in (1) as a control was measured. The fluorescence intensity of the control was converted at 30 μM TMR to calculate the amount of the TMR which was not adsorbed to the gelled casein carrier and left in the supernatant. Those results are shown in FIG. 3.

<Results>

Figure 3:
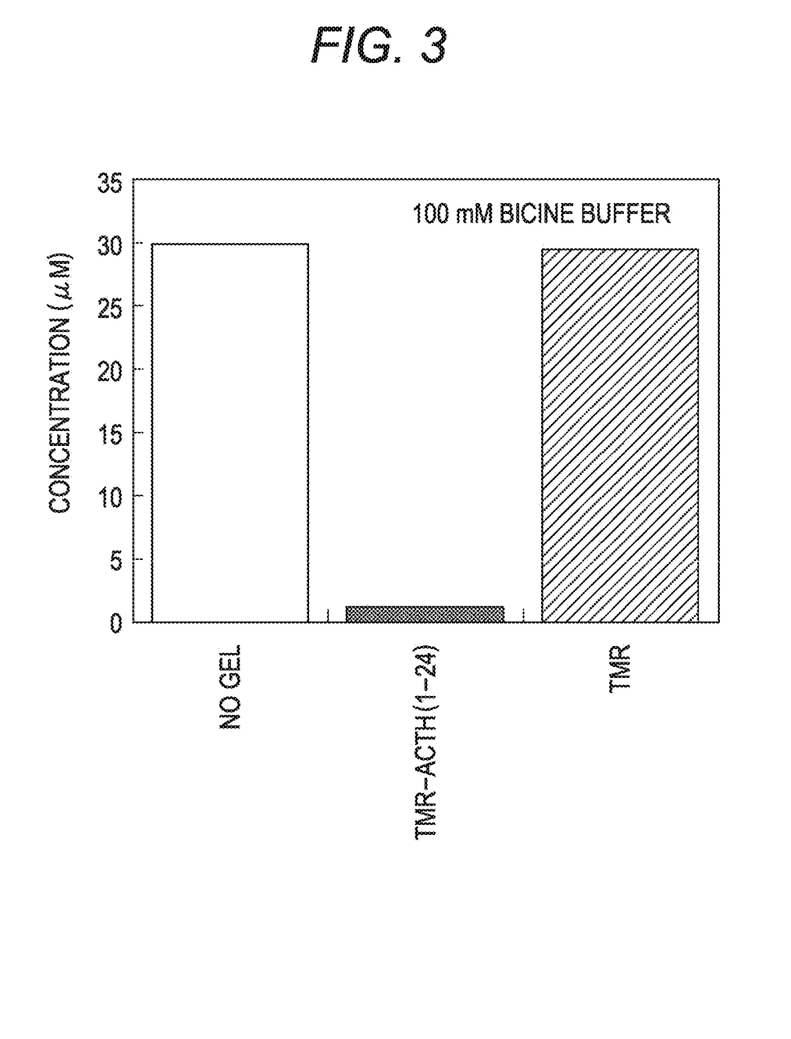
FIG. 3 is a graph showing that the gelled casein is adsorbed to the peptide portion in ACTH labeled with tetramethyl rhodamine (TMR)

From FIG. 3, it is found that the gelled casein carrier hardly adsorbs TMR. This showed that the gelled casein carrier selectively adsorbed the portion of ACTH (1-24) in TMR-labeled ACTH (1-24).

Example 4: Detection of ACTH (1-24) Adsorbed to Gelled Casein Carrier (1) Preparation of Samples
<Preparation of Sample A>

A solution of 300 μM TMR-labeled ACTH (1-24) (10 μL), 1 M Bicine buffer solution (pH 9) (10 μL), and ultrapure water (80 μL) were mixed to prepare a mixed solution (100 μL). The mixed solution thus prepared was collected as a sample A.

<Preparation of Sample B>

A 1 M Bicine buffer solution (pH 9) (10 μL) and ultrapure water (40 μL) were added to the 1% gelled casein carrier dispersion (50 μL) prepared in Example 1 to prepare a mixed solution (100 μL). The mixed solution was centrifuged at 22200 G for 3 minutes using the centrifuge to allow it to be separated into a supernatant and a precipitate. The resulting precipitate was collected as a sample B.

<Samples C and D>

The 1% gelled casein carrier dispersion (50 μL) prepared in Example 1 was mixed with a solution (10 μL) of 300 μM TMR-labeled ACTH (1-24). A 1 M Bicine buffer solution (pH 9) (10 μL) and ultrapure water (30 μL) were added thereto to prepare a mixed solution (100 μL). The final concentration of the gelled casein carrier in the mixed solution was adjusted to 0.5% and the final concentration of ACTH (1-24) was adjusted to 30 μM. The mixed solution was centrifuged at 22200 G for 3 minutes using the centrifuge to allow it to be separated into a supernatant and a precipitate. The supernatant was collected as a sample C. Subsequently, ultrapure water (100 μL) was added to the precipitate, which was stirred with a vortex. The mixed solution was centrifuged at 22200 G for 3 minutes using the centrifuge to allow it to be separated into a supernatant and a precipitate. The precipitate was collected as a sample D in SDS-PAGE shown in FIG. 4.

(2) Detection of ACTH (1-24) by SDS-PAGE

In advance, NuPAGE LDS Sample Buffer (4×) (manufactured by Invitrogen) (50 μL), NuPAGE Sample Reduction Agent (10×) (manufactured by Invitrogen) (20 μL), and ultrapure water (30 μL) were mixed to prepare a 2-fold condensed sample buffer (100 μL). Ultrapure water (20 μL) and 2-fold condensed sample buffer (20 μL) were added to the sample D collected in (1), which was heated at 70° C. for 10 minutes. After heating, the obtained sample was centrifuged at 22200 G for 3 minutes using the centrifuge to allow it to be separated into a supernatant and a precipitate. The supernatant (10 μL) obtained by centrifugation was subjected to SDS-PAGE. The sample B collected in (1) was subjected to the same operation as that of the sample D and SDS-PAGE. Further, a 2-fold condensed sample buffer (5 μL) was added to 5 μL of the sample A collected in (1), which was heated at 70° C. for 10 minutes. 10 μL of the resulting mixture was subjected to SDS-PAGE. The sample C collected in (1) was subjected to the same operation as that of the sample A and SDS-PAGE.

As an electrophoresis apparatus for SDS-PAGE, a vertical mini electrophoresis system (manufactured by Invitrogen) was used. As electrophoresis gels, NuPAGE 4-12% Bis-Tris Gels (1.0 mm, 10 wells, manufactured by Invitrogen) were used. As a running buffer, a solution prepared by 20-fold dilution of NuPAGE MES SDS running buffer (20×) (manufactured by Invitrogen) was used. The voltage during electrophoresis was set to a constant value of 200 V. After SDS-PAGE, the gel was stained with silver using EzStain Silver (ATTO CORPORATION). The results are shown in FIG. 4.

Figure 4:
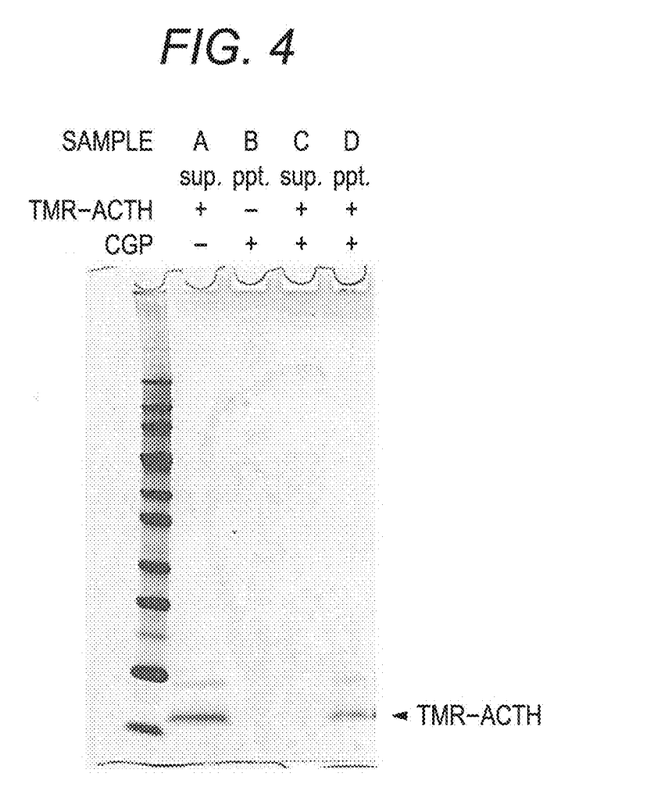
FIG. 4 shows a photograph when the ACTH adsorbed to the gelled casein is detected by SDS-PAGE and subsequent silver staining.

From the results of FIG. 4, almost all the ACTH (1-24) is adsorbed to the gelled casein carrier and is not present in the supernatant. The ACTH (1-24) adsorbed to the gelled casein carrier could be detected by directly subjecting it to SDS-PAGE. Generally, it is known that an ACTH molecule becomes a polymer in the presence of base. Accordingly, the bands present on the TMR-ACTH are expected to be ACTH polymers. It was found that the gelled casein carrier adsorbed to the polymer of ACTH (1-24).

Example 5: Removal of Albumin and Recovery of ACTH (1-24) From Complex to Which Albumin and ACTH (1-24) are Bound (Hereinafter Referred to as "BSA-ACTH (1-24) Complex")

(1) Preparation of Gelled Casein Carrier Dispersion

Casein sodium was dissolved in ultrapure water to prepare a 50 g/L (5%) casein sodium solution. A 5% water-soluble carbodiimide (WSC) solution (1 mL) and ultrapure water (3 mL) were added to the casein sodium solution (1 mL) to prepare a casein sodium-WSC mixed solution (5 mL) (final concentration of casein sodium: 1%, final concentration of WSC: 1%). The temperature of the mixed solution was returned to room temperature by heating at 80° C. for 10 minutes and a gel was formed in the mixed solution. The liquid portion was removed from the mixed solution containing the gel with a pipette. A gel precipitate was collected as a gelled casein carrier. Ultrapure water was added to the collected gelled casein carrier. The resulting mixture was centrifuged at 22200 G for 10 minutes using the centrifuge to allow it to be separated into a supernatant and a gel carrier, followed by removal of the supernatant with a pipette. The operation was repeatedly performed twice to wash the gelled casein carrier. The gel carrier after washing was made into a fine gel carrier by vortexing and pipetting and the resulting carrier was dispersed in ultrapure water (3 mL). The dispersion was a 1.6% gelled casein carrier dispersion.

(2) Preparation of BSA-ACTH (1-24) Complex

A 2400 μM BSA solution (40 μL), 200 μM TMR-labeled ACTH (1-24) (8 μL), and ultrapure water (32 μL) were mixed to prepare a BSA-ACTH (1-24) complex solution (80 μL). The concentration of BSA in the solution is 1200 μM, and the concentration of TMR-labeled ACTH (1-24) was adjusted to 20 μM. The equilibrium dissociation constant (Kd) between BSA and TMR-labeled ACTH (1-24) was measured by the fluorescence titration method and the Kd value was 12 μM. That is, when the prepared complex solution is 2-fold diluted, the concentration of BSA is 600 μM. When the concentration of TMR-labeled ACTH (1-24) is 10 μM, 98.0% of TMR-labeled ACTH (1-24) forms a complex with BSA.

(3) Preparation of Mixed Solution of Gelled Casein Carrier and Sample

<Preparation of Mixed Solution of Gelled Casein Carrier and BSA-ACTH (1-24) Complex>

The solution (80 μL) prepared in (2) was mixed with the 1.6% gelled casein carrier dispersion (50 μL) prepared in (1). Thereafter, a 1 M Bicine/NaOH buffer solution (pH 9) (16 μL) and ultrapure water (14 μL) were added thereto to prepare a mixed solution (160 μL). The mixed solution was centrifuged at 22200 G for 3 minutes using the centrifuge to allow it to be separated into a supernatant and a gelled casein carrier. The gelled casein carrier was subjected to the following operation (4). The supernatant was used as a "supernatant A" of a sample containing BSA. Further, a mixed solution not containing the gelled casein carrier, a BSA-ACTH (1-24) complex solution (80 μL), a 1 M Bicine/NaOH buffer solution (pH 9) (16 μL), and ultrapure water (64 μL) were added to prepare a mixed solution (160 μL) as a control. The solution was used as a reference (REF.) sample containing BSA.

<Preparation of Mixed Solution of Gelled Casein Carrier and ACTH (1-24)>

A mixed solution was prepared in the same manner as described in the preparation of mixed solution of gelled casein carrier and BSA-ACTH (1-24) complex using a 20 μM TMR-labeled ACTH (1-24) solution in place of the BSA-ACTH (1-24) complex solution. The gelled casein carrier was subjected to the following operation (4). The supernatant was used as a "supernatant A" of a sample not containing BSA. Further, a mixed solution not containing the gelled casein carrier, 20 mM TMR-labeled ACTH (1-24) (80 μL), a 1 M Bicine/NaOH buffer solution (pH 9, 16 μL), and ultrapure water (64 μL) were added to prepare a mixed solution (160 μL) as a control. The solution was used as a REF. sample not containing BSA.

(4) Washing of Gelled Casein Carrier

<Washing of Gelled Casein Carrier Mixed with BSA-ACTH (1-24) Complex>

A 20 mM Bicine/NaOH buffer solution (160 μL) was added to the gelled casein carrier separated in (3) Preparation of mixed solution of gelled-casein carrier and BSA-ACTH (1-24) complex. The mixture was pipetted so that the gelled casein carrier was uniformly dispersed in the solution. After pipetting, the resulting dispersion was centrifuged at 22200 G for 5 minutes using the centrifuge to allow it to be separated into a supernatant and a gelled casein carrier. The gelled casein carrier was subjected to the following operation (5). The supernatant was used as a "supernatant B" of a sample containing BSA.

<Washing of Gelled Casein Carrier Mixed with ACTH (1-24)>

A 20 mM Bicine/NaOH buffer solution (160 μL) was added to the gelled casein carrier separated in (3) Preparation of mixed solution of gelled-casein carrier and ACTH (1-24). The mixture was pipetted so that the gelled casein carrier was uniformly dispersed in the solution. After pipetting, the resulting dispersion was centrifuged at 22200 G for 5 minutes using the centrifuge to allow it to be separated into a supernatant and a gelled casein carrier. The gelled casein carrier was subjected to the following operation (5). The supernatant was used as a "supernatant B" of a sample not containing BSA.

(5) Release of ACTH (1-24) Adsorbed to Gelled Casein Carrier

<Release of ACTH (1-24) from Gelled Casein Carrier in Contact with BSA-ACTH (1-24) Complex>

A 100 mM MES/NaOH buffer solution (pH 5) (160 μL) was added to the gelled casein carrier after the process in (4) Washing of gelled casein carrier mixed with BSA-ACTH (1-24) complex. The mixture was pipetted so that the gelled casein carrier was uniformly dispersed in the solution. After pipetting, the mixed solution was centrifuged at 22200 G for 3 minutes using the centrifuge to allow it to be separated into a supernatant and a gelled casein carrier. The supernatant was used as a "supernatant C" of a sample containing BSA.

<Release of ACTH (1-24) Adsorbed to Gelled Casein Carrier Mixed with ACTH (1-24)>

A 100 mM MES/NaOH buffer solution (pH 5) (160 μL) was added to the gelled casein carrier after the process in (4) Washing of gelled casein carrier mixed with ACTH (1-24). The mixture was pipetted so that the gelled casein carrier was uniformly dispersed in the solution. After pipetting, the mixed solution was centrifuged at 22200 G for 3 minutes using the centrifuge to allow it to be separated into a supernatant and a gelled casein carrier. The supernatant was used as a "supernatant C" of a sample not containing BSA.

(6) Confirmation of State of Recovery of ACTH (1-24) with Gelled Casein Carrier by SDS-PAGE In advance, a 10× Loading Buffer (10 μL, manufactured by TAKARA), a 60% glycerol solution (5 μL), and ultrapure water (85 μL) were mixed to prepare a solution. The resulting solution was used as a sample buffer. Then, 20 μL of the REF. sample containing BSA, 20 μL of the sample supernatants A to C containing BSA, 20 μL of the REF. sample not containing BSA, and 20 μL of the sample supernatants A to C not containing BSA were collected. Each of the solutions was mixed with the sample buffer (2 μL), followed by SDS-PAGE. As an electrophoresis apparatus for SDS-PAGE, a vertical mini electrophoresis system (manufactured by Invitrogen) was used. As electrophoresis gels, NuPAGE 4-12% Bis-Tris Gels (1.0 mm, 10 wells, manufactured by Invitrogen) were used. As a running buffer, a solution prepared by 20-fold dilution of NuPAGE MES SDS running buffer (20×) (manufactured by Invitrogen) was used. The voltage during electrophoresis was set to a constant value of 200 V. Thus, after performing the SDS-PAGE, image data of electrophoresis gels (FIG. 5) was obtained in the High Sample Intensity mode at the wavelength for TAMRA (excitation wavelength: 532 nm) of a fluorescence imager (Pharos FX (trademark) Molecular Imager: BIO-RAD LABORATORIES). Thereafter, the electrophoresis gels were stained with silver according to the procedure using EzStain Silver (ATTO CORPORATION) (FIG. 6).

<Results of SDS-PAGE>

Figure 5:
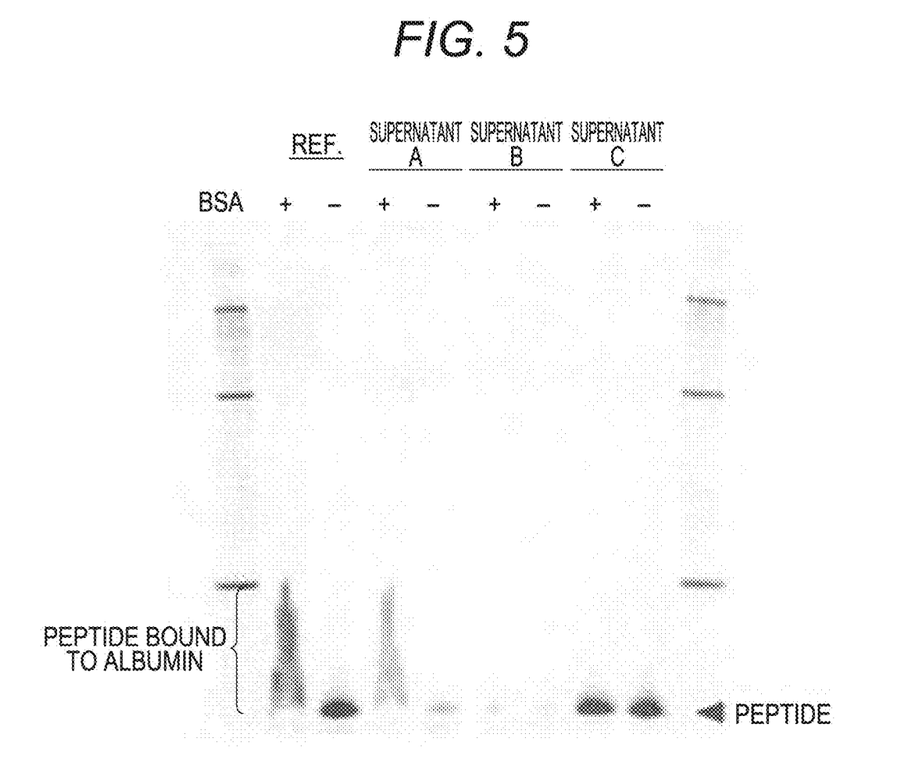
FIG. 5 shows a photograph when the ACTH forming a complex with albumin, which is adsorbed to the gelled casein, is detected by SDS-PAGE and subsequent fluorescence imaging.
Figure 6:
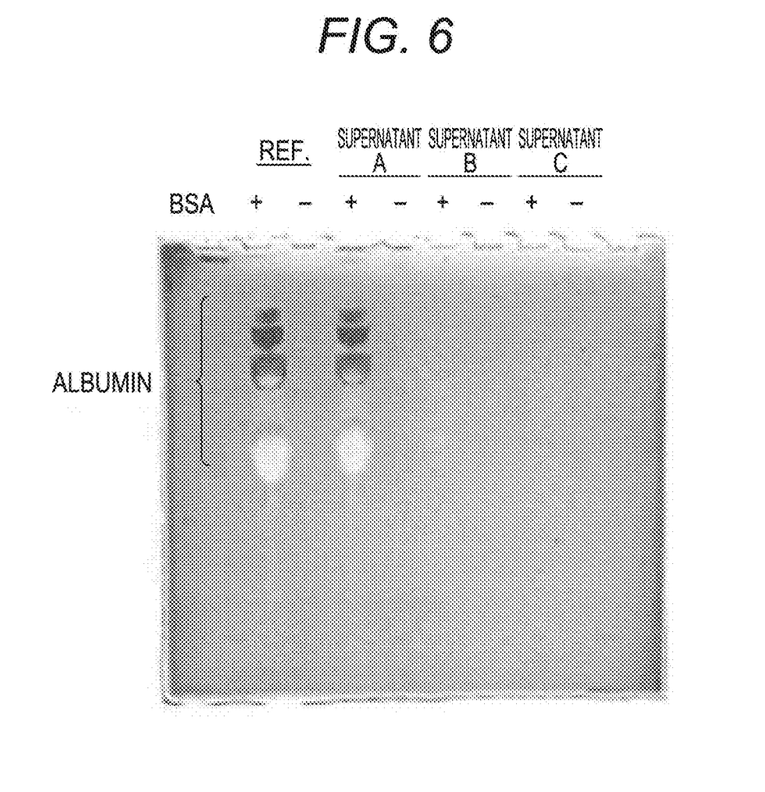
FIG. 6 shows a photograph when the fact that the gelled casein is not adsorbed to albumin is confirmed by SDS-PAGE and subsequent silver staining.

The bands of TMR-labeled ACTH (1-24) can be confirmed from FIG. 5. The bands of BSA can be confirmed from FIG. 6. In the mixed series (series containing BSA) prepared by mixing the gelled casein carrier and the BSA-ACTH (1-24) complex, the results of the REF. sample of FIG. 6 and the sample (the supernatant A) show that BSA is not adsorbed to the gelled casein carrier in the presence of the Bicine/NaOH buffer solution (pH 9). However, when smear bands of TMR-labeled ACTH (1-24) are confirmed in FIG. 5, the density of the bands is decreased. Thus, it is considered that a part of the TMR-ACTH (1-24) is detached from the BSA and adsorbed to the gelled casein carrier. It is surmised that the proportion in which the gelled casein carrier adsorbs TMR-ACTH (1-24) from BSA is determined by the balance between the equilibrium reaction of BSA and ACTH (1-24) and the equilibrium reaction of the gelled casein carrier and ACTH (1-24). In other words, in order to collect a larger amount of TMR-ACTH (1-24) from BSA, it is necessary to increase the additive amount of the gelled casein carrier. In the sample (the supernatant B), the band of TMR-labeled ACTH (1-24) can be hardly confirmed. Thus, it is expected that TMR-labeled ACTH (1-24) is still adsorbed to the gelled casein carrier in the washing process. In the sample (the supernatant C), the dark bands of TMR-labeled ACTH (1-24) can be confirmed. Accordingly, it was found that the TMR-labeled ACTH (1-24) was released from the gelled casein carrier in the presence of the MES/NaOH buffer solution (pH 5).

The above results suggested that even the ACTH (1-24) bound to BSA could be adsorbed to the gelled casein carrier. From the result, it was suggested that the ACTH (1-24) could be recovered by removing BSA from the BSA-ACTH (1-24) complex using the gelled casein.

Example 6: Examination of Conditions for Dissociating ACTH (1-24) From Gelled Casein Carrier (1) Preparation of Gelled Casein Carrier Dispersion A 1% gelled casein carrier dispersion was prepared in the same manner as described in (1) Preparation of gelled casein carrier dispersion of Example 1.

(2) Preparation of Mixed Solution of Gelled Casein Carrier, Sample, and ACTH (1-24)

The 1% gelled casein carrier dispersion (50 μL) prepared in (1) was mixed with a 300 μM TMR-labeled ACTH (1-24) solution (10 μL), and a 1 M Bicine buffer solution (pH 9) (10 μL) and ultrapure water (30 μL) were added thereto to prepare a mixed solution (100 μL). The final concentration of the gelled casein carrier in the mixed solution was adjusted to 0.5% and the final concentration of TMR-labeled ACTH (1-24) was adjusted to 30 μM. The mixed solution was centrifuged at 22200 G for 3 minutes using the centrifuge to allow it to be separated into a supernatant and a gelled casein carrier.

(3) Washing of Gelled Casein Carrier Mixed with ACTH (1-24)

A 20 mM Bicine/NaOH buffer solution (160 μL) was added to the gelled casein carrier separated in (2), followed by pipetting of the gelled casein carrier. After pipetting, the resulting dispersion was centrifuged at 22200 G for 5 minutes using the centrifuge to allow it to be separated into a supernatant and a gelled casein carrier.

(4) Dissociation of ACTH (1-24) Bound to Gelled Casein Carrier

Each solution with each pH shown in Table 2 was added to the gelled casein carrier washed in (3). The mixture was pipetted so that the gelled casein carrier was uniformly dispersed therein. After pipetting, the mixed solution was centrifuged at 22200 G for 3 minutes using the centrifuge to allow it to be separated into a supernatant and a gelled casein carrier. In order to calculate the concentration of ACTH (1-24) remained in the separated supernatant, the fluorescence intensity of the supernatant was measured by the same operation as the spectrophotofluorometric measurement described in (3) of Example 3. As a control for comparison with the mixed solutions, a 30 μM TMR-labeled ACTH (1-24) solution containing each solution with each pH shown in Table 2 and not containing the gelled casein carrier was prepared. The fluorescence intensity of the solution was calculated in the same manner as described above. The fluorescence intensity of the control was converted at 30 μM TMR-labeled ACTH (1-24) to calculate the concentration of ACTH (1-24) remained in the supernatant from which the gelled casein carrier was removed. The measurement results are shown in Table 2 and FIG. 7.

TABLE 2

| Solution | pH | Concentration of ACTH (1-24) in the supernatant [μM] (not containing the gelled casein carrier) | Concentration of ACTH (1-24) in the supernatant [μM] (after dissociation from the gelled casein carrier) |
|---|---|---|---|
| 100 mM Glycine/HCl buffer solution | 2.5 | 30 | 27.8 |
| Only HCl | 2.5 | 30 | 31.1 |
| Only HCl | 3.9 | 30 | 25.2 |
| 10 mM acetic acid solution | 4.1 | 30 | 30.0 |
| 30 mM MES solution | 4.5 | 30 | 27.2 |
| 100 mM sodium acetate buffer solution | 4.9 | 30 | 18.9 |
| 30 mM MES solution | 4.9 | 30 | 25.7 |
| 100 mM MES/NaOH buffer solution | 5.1 | 30 | 18.1 |
| Only HCl | 5.3 | 30 | 19.1 |
| 30 mM MES solution* | 6 | 30 | 10.5 |
| 30 mM MES solution* | 7.2 | 30 | 6.7 |
| 100 mM PBS buffer solution | 7.3 | 30 | 1 |

TABLE 2-continued

| Solution | pH | Concentration of ACTH (1-24) in the supernatant [μM] (not containing the gelled casein carrier) | Concentration of ACTH (1-24) in the supernatant [μM] (after dissociation from the gelled casein carrier) |
|---|---|---|---|
| Only HCl | 7.7 | 30 | 0.8 |
| 30 mM ammonium bicarbonate solution | 8.3 | 30 | 7.9 |
| Only NaOH | 8.4 | 30 | 1.1 |
| 100 mM Bicine/NaOH buffer solution | 8.8 | 30 | 0.8 |
| 100 mM CAPS/NaOH buffer solution | 10.3 | 30 | 3.2 |

*The pH of the 30 mM MES solution was adjusted with HCl and NaOH.

Figure 7:
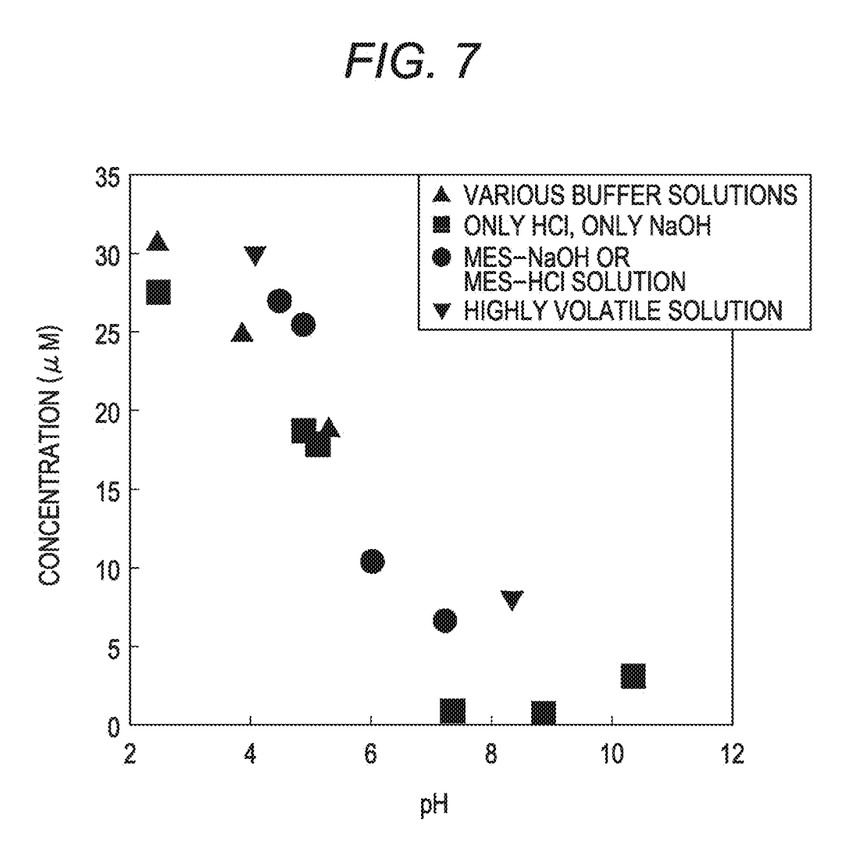
FIG. 7 is a graph showing that an affinity of the gelled casein for ACTH varies depending on the pH.

From Table 2 and FIG. 7, it was found that the ACTH (1-24) bound to the gelled casein carrier could be dissociated from the gelled casein carrier by using a solution having a pH of 5 or less regardless of the type of the solution. The 10 mM acetic acid solution and 30 mM ammonium bicarbonate solution used as pH adjustors are volatile. Thus, it is known that, in HPLC measurement or MS measurement, it is possible to perform a direct measurement without a process of demineralization. In other words, an appropriate solvent can be selected according to the measurement procedure of the solution after dissociation. For example, when ACTH (1-24) is detected by a biochemical procedure, a Glycine/NaOH buffer solution which is a Good's buffer or a MES/NaOH buffer solution may be used. In the case of a procedure which requires the process of demineralization before the treatment like the mass spectrometry, ACTH (1-24) can be dissociated using a volatile pH adjuster such as an acetic acid solution.

Example 7: Removal of Albumin and Recovery of ACTH (1-24) From Serum Containing TMR-Labeled ACTH (1-24)

(1) Preparation of Gelled Casein Carrier Dispersion

A 1% gelled casein carrier dispersion was prepared in the same manner as described in (1) Preparation of gelled casein carrier dispersion of Example 1.

(2) Preparation of Mixed Solution of Gelled Casein Carrier and Sample

<Preparation of Mixed Solution of Gelled Casein Carrier and Serum Containing TMR-Labeled ACTH (1-24)>

Serum previously collected from healthy woman (22 years old) (100 μL, PROMEDDX "Normal Serum Pool") was mixed with 300 μM TMR-labeled ACTH (1-24) (10 μL) to prepare serum containing TMR-labeled ACTH (1-24). The 1% gelled casein carrier dispersion (100 μL) prepared in (1) was placed in another container and centrifuged to allow the dispersion to be separated into a supernatant and a precipitate. The supernatant was removed with a pipette and only the precipitate was collected. Then, the serum containing TMR-labeled ACTH (1-24) prepared above (110 μL), a 1 M Bicine buffer solution (pH 9) (20 μL), and ultrapure water (20 μL) were added to the obtained precipitate to prepare a mixed solution (150 μL) of the gelled casein carrier and the sample. The final concentration of the gelled casein carrier in the mixed solution was adjusted to 0.75%, the final concentration of TMR-labeled ACTH (1-24) was adjusted to 20 μM, and the dilution ratio of the serum was adjusted to 1.5-fold. The mixed solution was centrifuged at 22200 G for 3 minutes using the centrifuge to allow it to be separated into a supernatant and a gelled casein carrier. As a reference sample before recovery not containing the gelled casein carrier, a mixed solution (150 μL) was prepared by adding serum containing the TMR-labeled ACTH (1-24) (110 μL), a 1 M Bicine buffer solution (pH 9) (20 μL), and ultrapure water (20 μL).

<Preparation of Solution Containing Only Gelled Casein Carrier>

A gelled casein carrier solution was prepared by the same operation as described in Preparation of mixed solution of gelled casein carrier and serum containing TMR-labeled ACTH (1-24) except that ultrapure water was used in place of the serum containing TMR-labeled ACTH (1-24). The solution was used as a control sample A. As a reference sample before recovery not containing the gelled casein carrier, a mixed solution (150 μL) was prepared by adding a 1 M Bicine buffer solution (pH 9) (20 μL) and ultrapure water (130 μL).

<Preparation of Mixed Solution of Gelled Casein Carrier and Serum Solution>

A mixed solution of the gelled casein carrier and serum was prepared by the same operation as described in Preparation of mixed solution of gelled casein carrier and serum containing TMR-labeled ACTH (1-24) except that ultrapure water was used in place of the TMR-labeled ACTH (1-24). The solution was used as a control sample B. As a reference sample before recovery not containing the gelled casein carrier, a mixed solution (150 μL) was prepared by adding serum (100 μL), a 1 M Bicine buffer solution (pH 9) (20 μL), and ultrapure water (30 μL).

(3) Washing of Gelled Casein Carrier

The supernatant separated in (2) Preparation of mixed solution was removed with a pipette and the gelled casein carrier was collected. A 20 mM Bicine/NaOH buffer solution (150 μL) was added to the gelled casein carrier, followed by pipetting of the gelled casein carrier. The resulting solution was centrifuged at 22200 G for 5 minutes using the centrifuge to allow it to be separated into a supernatant and a gelled casein carrier. The operation was repeatedly performed twice. The same operation was performed on the controls A and B prepared in (2).

(4) Release of ACTH (1-24) Adsorbed to Gelled Casein Carrier

A 100 mM MES/NaOH buffer solution (pH 5) (50 μL) was added to the gelled casein carrier after the process of (3) Washing of gelled casein carrier, followed by pipetting of the gelled casein carrier. The mixed solution was centrifuged at 22200 G for 3 minutes using the centrifuge to allow it to be separated into a supernatant and a gelled casein carrier. The supernatant was recovered with a pipette and it was used as a recovered sample. The same operation was performed on the samples of the controls A and B.

(5) Confirmation of Removal of Serum Component and Recovery of ACTH (1-24) by SDS-PAGE In advance, NuPAGE LDS Sample Buffer (4×) (manufactured by Invitrogen) (50 μL), NuPAGE Sample Reduction Agent (10×) (manufactured by Invitrogen) (20 μL), and ultrapure water (30 μL) were mixed to prepare a 2-fold condensed sample buffer (100 μL). Ultrapure water (5 μL) and 2-fold condensed sample buffer (5 μL) were added to the reference sample before recovery which was collected in (2), and the resulting mixture was heated at 70° C. for 10 minutes. Similarly, 2-fold condensed sample buffer (5 μL) was respectively added to the reference sample before recovery for the control samples A and B which were collected in (2), the sample after recovery which was collected in (4), and the sample after recovery for the control samples A and B, followed by heating at 70° C. for 10 minutes to prepare samples. Each of the obtained samples (1 µL) was subjected to SDS-PAGE. The electrophoresis apparatus for SDS-PAGE, the electrophoresis gels, and the running buffer are the same as those of Example 4 (2). The voltage during electrophoresis was set to a constant value of 200 V. After SDS-PAGE, fluorescence images and silver-stained images were obtained by the same operation as that of Example 5 (6). The results are shown in FIG. 8.

Figure 8:
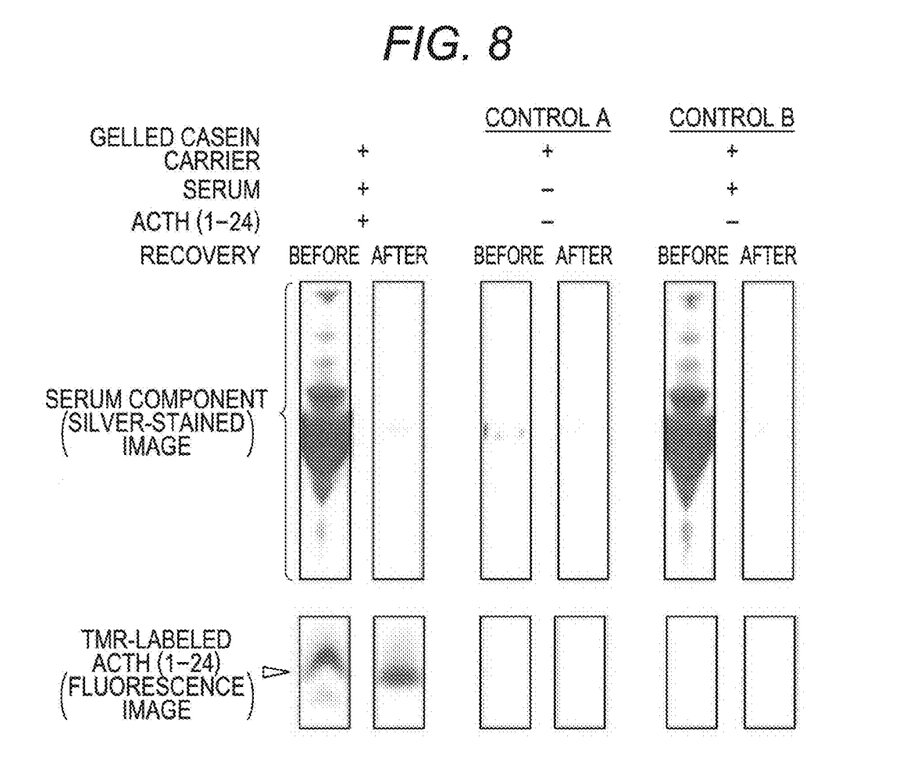
FIG. 8 shows a photograph in which the fact that ACTH in the serum can be detected by the method for detecting ACTH of the present invention is shown by SDS-PAGE, subsequent silver staining, and fluorescence imaging.

From the results of FIG. 8, it was confirmed that the proteins in the serum were hardly adsorbed to the gelled casein carrier and ACTH (1-24) could be selectively recovered from the serum.

Example 8: Removal of Protein and Recovery of ACTH (1-24) From Urine Containing TMR-Labeled ACTH (1-24)

(1) Preparation of Gelled Casein Carrier Fluid Concentrate

A 1% gelled casein carrier fluid concentrate was prepared in the same manner as described in (1) Preparation of gelled casein carrier fluid concentrate of Example 1 (1).

(2) Preparation of Mixed Solution of Gelled Casein Carrier and Sample

<Preparation of Mixed Solution of Gelled Casein Carrier and Urine Containing TMR-Labeled ACTH (1-24)>

Normal urine previously collected from a single donor (100 µL, ProMedDx) was mixed with 300 µM TMR-labeled ACTH (1-24) (10 µL) to prepare urine containing TMR-labeled ACTH (1-24). The 1% gelled casein carrier fluid concentrate (60 µL) prepared in (1) was placed in another container and centrifuged to allow the dispersion to be separated into a supernatant and a precipitate. The supernatant was removed with a pipette and only the precipitate was collected. Then, the urine (110 µL) containing TMR-labeled ACTH (1-24) prepared above and a 1 M Bicine buffer solution (pH 9) (10 µL) were added to the obtained precipitate to prepare a mixed solution (120 µL) of the gelled casein carrier and the sample. The final concentration of the gelled casein carrier in the mixed solution was adjusted to 0.5%, the final concentration of TMR-labeled ACTH (1-24) was adjusted to 25 µM, and the dilution rate of the urine was adjusted to 1.2-fold. The mixed solution was centrifuged at 22200 G for 3 minutes using the centrifuge to allow it to be separated into a supernatant and a gelled casein carrier. As a reference sample before recovery not containing the gelled casein carrier, a mixed solution (120 µL) was prepared by adding the urine containing TMR-labeled ACTH (1-24) (110 µL) and a 1 M Bicine buffer solution (pH 9) (10 µL).

<Preparation of Solution Containing Only Gelled Casein Carrier>

A gelled casein carrier solution was prepared by the same operation as described in Preparation of mixed solution of gelled casein carrier and urine containing TMR-labeled ACTH (1-24) except that ultrapure water was used in place of the urine containing TMR-labeled ACTH (1-24). The solution was used as a control sample A. As a reference sample before recovery not containing the gelled casein carrier, a mixed solution (120 µL) was prepared by adding a 1 M Bicine buffer solution (pH 9) (10 µL) and ultrapure water (110 µL).

<Preparation of Mixed Solution of Gelled Casein Carrier and Urine>

A mixed solution of the gelled casein carrier and urine was prepared by the same operation as described in Preparation of mixed solution of gelled casein carrier and urine containing TMR-labeled ACTH (1-24) except that ultrapure water was used in place of TMR-labeled ACTH (1-24). The solution was used as a control sample B. As a reference sample before recovery not containing the gelled casein carrier, a mixed solution (120 µL) was prepared by adding urine (100 µL), a 1 M Bicine buffer solution (pH 9) (10 µL), and ultrapure water (10 µL).

<Preparation of Mixed Solution of Gelled Casein Carrier and TMR-Labeled ACTH (1-24)>

A mixed solution of the gelled casein carrier and TMR-labeled ACTH (1-24) was prepared by the same operation as described in Preparation of mixed solution of gelled casein carrier and urine containing TMR-labeled ACTH (1-24) except that ultrapure water was used in place of the urine. The solution was used as a control sample C. As a reference sample before recovery not containing the gelled casein carrier, a mixed solution (120 µL) was prepared by adding 300 µM TMR-labeled ACTH (1-24) (10 µL), a 1 M Bicine buffer solution (pH 9) (10 µL), and ultrapure water (100 µL).

(3) Washing of Gelled Casein Carrier

The supernatant separated in (2) Preparation of mixed solution was removed with a pipette and the gelled casein carrier was collected. A 20 mM Bicine/NaOH buffer solution (120 µL) was added to the gelled casein carrier, followed by pipetting of the gelled casein carrier. The resulting solution was centrifuged at 22200 G for 5 minutes using the centrifuge to allow it to be separated into a supernatant and a gelled casein carrier. The operation was repeatedly performed twice. The same operation was performed on the control samples A to C prepared in (2).

(4) Release of ACTH (1-24) Adsorbed to Gelled Casein Carrier

A 100 mM Glycine/NaOH buffer solution (pH 2.5) (60 µL) was added to the gelled casein carrier after the process of (3) Washing of gelled casein carrier, followed by pipetting of the gelled casein carrier. The mixed solution was centrifuged at 22200 G for 3 minutes using the centrifuge to allow it to be separated into a supernatant and a gelled casein carrier. The supernatant was recovered with a pipette and it was used as a recovered sample. The same operation was performed on the control samples A to C.

(5) Confirmation of Removal of Urine Component and Recovery of ACTH (1-24) by SDS-PAGE In advance, NuPAGE LDS Sample Buffer (4×) (manufactured by Invitrogen) (50 µL), NuPAGE Sample Reduction Agent (10×) (manufactured by Invitrogen) (20 µL), and ultrapure water (30 µL) were mixed to prepare a 2-fold condensed sample buffer (100 µL). Ultrapure water (5 µL) and 2-fold condensed sample buffer (5 µL) were added to the reference sample before recovery which was collected in (2), and the resulting mixture was heated at 70° C. for 10 minutes. Similarly, 2-fold condensed sample buffer (5 µL) was respectively added to the reference sample before recovery for the control samples A to C which were collected in (2), the sample after recovery which was collected in (4), and the sample after recovery for the control samples A to C, followed by heating at 70° C. for 10 minutes to prepare samples. Each of the obtained samples (10 µL) was subjected to SDS-PAGE.

Figure 9:
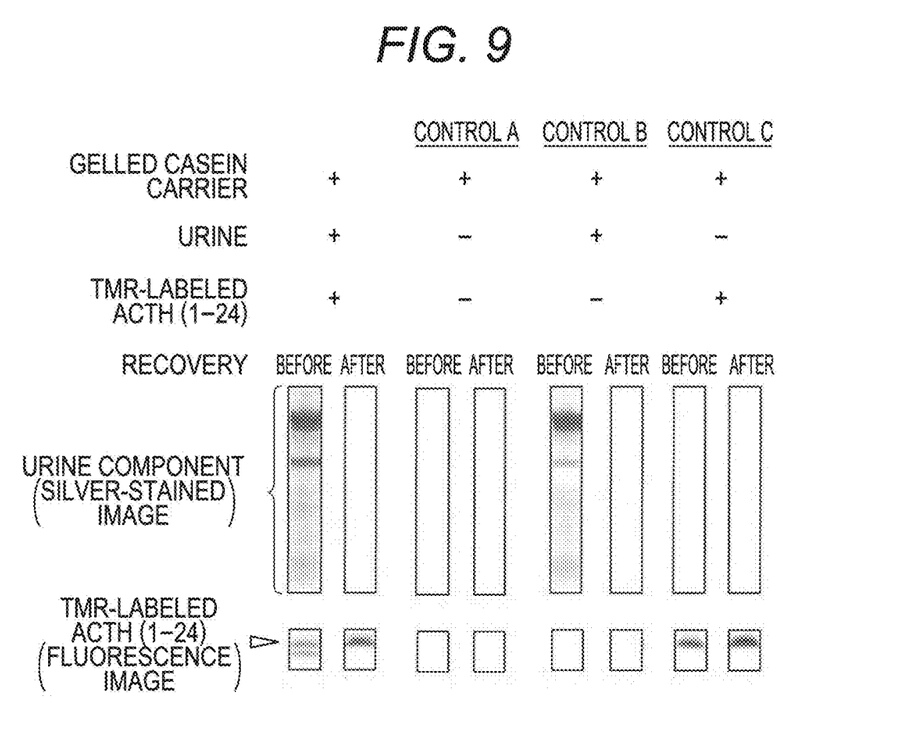
FIG. 9 shows a photograph in which the fact that ACTH in the urine can be detected by the method for detecting ACTH of the present invention is shown by SDS-PAGE, subsequent silver staining, and fluorescence imaging.

The electrophoresis apparatus for SDS-PAGE, the electrophoresis gels, and the running buffer are the same as those of Example 4 (2). The voltage during electrophoresis was set to a constant value of 200 V. After SDS-PAGE, fluorescence images and silver-stained images were obtained by the same operation as that of Example 5 (6). The results are shown in FIG. 9. From the results of FIG. 9, it was confirmed that the proteins in the urine were hardly adsorbed to the gelled casein carrier and ACTH (1-24) could be selectively recovered from the urine.

What is claimed is:

1. A method for detecting adrenocorticotropic hormone comprising the steps of:
   bringing a liquid sample containing adrenocorticotropic hormone into contact with gelled casein to adsorb adrenocorticotropic hormone to the gelled casein;
   recovering the gelled casein brought into contact with the liquid sample;
   allowing the adrenocorticotropic hormone adsorbed to the recovered gelled casein to be released from the gelled casein; and
   detecting the adrenocorticotropic hormone released from the gelled casein.

2. The method according to claim 1, wherein the bringing step is performed by bringing the liquid sample into contact with the gelled casein in the range of pH 6.5 or more.

3. The method according to claim 1, wherein the allowing step is performed by bringing the recovered gelled casein into contact with an aqueous medium at a pH 5.5 or less and allowing the adrenocorticotropic hormone adsorbed to the gelled casein to be released into the aqueous medium.

4. The method according to claim 1, wherein the gelled casein is casein gelled with a crosslinker.

5. The method according to claim 4, wherein the crosslinker is water-soluble carbodiimide.

6. The method according to claim 1, wherein the liquid sample is blood, plasma, serum or urine.

7. The method according to claim 1, wherein the recovering the gelled casein is performed by centrifuging the liquid sample contacting the gelled casein, and removing a supernatant.

* * * * *

SEQUENCE LISTING

<160> NUMBER OF SEQ ID NOS: 4

<210> SEQ ID NO 1
<211> LENGTH: 24
<212> TYPE: PRT
<213> ORGANISM: Homo sapiens

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 2
<211> LENGTH: 21
<212> TYPE: PRT
<213> ORGANISM: Homo sapiens

<400> SEQUENCE: 2

Asn Val His Ser Ala Gly Ala Ala Gly Ser Arg Met Asn Phe Arg Pro
1               5                   10                  15

Gly Val Leu Ser Ser
            20

<210> SEQ ID NO 3
<211> LENGTH: 25
<212> TYPE: PRT
<213> ORGANISM: Homo sapiens

<400> SEQUENCE: 3

Asp Glu Ala Gly Ser Glu Ala Asp His Glu Gly Thr His Ser Thr Lys
1               5                   10                  15

Arg Gly His Ala Lys Ser Arg Pro Val
            20                  25

<210> SEQ ID NO 4
<211> LENGTH: 25
<212> TYPE: PRT
<213> ORGANISM: Homo sapiens

<400> SEQUENCE: 4

Ala Val Pro Pro Asn Asn Ser Asn Ala Ala Glu Asp Asp Leu Pro Thr
1               5                   10                  15

Val Glu Leu Gln Gly Val Val Pro Arg
            20                  25